United States Patent [19]
Clemente et al.

[11] Patent Number: 6,126,967
[45] Date of Patent: Oct. 3, 2000

[54] EXTENDED RELEASE ACETAMINOPHEN PARTICLES

[75] Inventors: Emmett Clemente, Manchester; Aloysius O. Anaebonam, Burlington; Robert W. Mendes, Dedham; Abdel A. Fawzy, Dracut; Eric M. Morrel, Medfield, all of Mass.

[73] Assignee: Ascent Pediatrics, Wilmington, Mass.

[21] Appl. No.: 09/146,248

[22] Filed: Sep. 3, 1998

[51] Int. Cl.[7] ................................ A61K 9/62; A61K 9/16
[52] U.S. Cl. .................... 424/461; 424/451; 424/456; 424/458; 424/459; 424/462; 424/489; 424/490; 424/493; 424/494; 424/495; 424/497; 514/964; 514/965
[58] Field of Search ....................... 424/451, 456, 424/457, 458, 461, 462, 489, 493, 494, 495, 497; 514/964, 965

[56] References Cited

U.S. PATENT DOCUMENTS

| | | | |
|---|---|---|---|
| 4,820,522 | 4/1989 | Radebaugh et al. | 424/468 |
| 4,867,984 | 9/1989 | Patel . | |
| 4,874,613 | 10/1989 | Hsiao . | |
| 4,952,402 | 8/1990 | Sparks et al. | 424/419 |
| 4,983,401 | 1/1991 | Eichel et al. . | |
| 5,026,559 | 6/1991 | Eichel et al. . | |
| 5,032,384 | 7/1991 | Yeh et al. | 424/49 |
| 5,773,031 | 6/1998 | Shah et al. . | |
| 5,780,055 | 7/1998 | Habib et al. . | |

OTHER PUBLICATIONS

S.C. Porter, "Coating of Pharmecutical Dosage Forms," *Remington's Pharmeceutical Sciences*, 18th ed., A.R. Gonnaro ed., Chapter 90, Mack Publishing Co., Easton, PA (1990) pp. 1666–1675.

M.D. Rawlins, et al., Eur. J. Clin. Pharmacol., 11:283–286 (1977).

R. Langer, Science, 249:1527–1533 (1990).

*Primary Examiner*—Thurman K. Page
*Assistant Examiner*—Brian K. Seidleck
*Attorney, Agent, or Firm*—Welsh & Katz, Ltd.

[57] ABSTRACT

An extended release acetaminophen composition comprises a plurality of discrete particles containing acetaminophen which, when contained within a gelatin capsule and assayed in a USP Apparatus I rotating basket at 50 rpm in 900 mL of phosphate buffer at pH 5.8 and 37° C., exhibits about 40 percent to about 53 percent acetaminophen dissolution at one-half hour, about 50 percent to about 68 percent dissolution at 45 minutes, about 57 percent to about 77 percent acetaminophen dissolution at one hour, and about 82 percent to about 92 percent acetaminophen dissolution at two hours. After six hours, the contemplated extended release acetaminophen composition exhibits substantially complete dissolution. A process for treating a human patient with the extended release acetaminophen composition is also disclosed.

18 Claims, 4 Drawing Sheets

EXTENDED RELEASE ACETAMINOPHEN PARTICLES

FIELD OF THE INVENTION

This invention relates to the extended release administration of medication. More particularly, the invention relates to an acetaminophen composition that has particular in vitro acetaminophen release characteristics and is adapted for use by human patients that have difficulty swallowing acetaminophen tablets or capsules.

BACKGROUND OF THE INVENTION

Coating medication to effect a controlled or extended release administration profile is well known in the art. Drug manufacturers have been using such methods to provide oral administration of medications that enter the body over a predetermined, extended period of time.

Controlled release administration provides many benefits to a patient. For example, controlled release administration can reduce the number of times that a patient is required to self-administer medication, thus reduce the possibility that the patient will forget to take his or her medication during the day Analgesics and antipyretics, such as acetaminophen are often self-administered over the course of a day to help alleviate pain or fever from which a person is suffering. Often, such symptoms can last for long periods of time. However, the symptoms need not affect the person's typical daily routine. Thus, the person may not remember to take his or her medication because of other daily activities.

As a result, it has become advantageous to provide an extended or controlled release analgesic drug for self-administration. Such controlled release administration can substantially reduce the number of times that a patient takes medication during the day. The controlled release properties also facilitate night time administration in that a controlled release coating can be provided to sufficiently extend over the period during which the person is asleep.

In preparing and applying a controlled or extended release coating it is known to prepare the medication as a quantity of small pellets, non-pareils or prills, which are small, generally spherically shaped form of the medication. The prills are coated with, for example, an aqueous, ethyl-cellulose based film coating product, which dissolves when subjected to humidity or liquid aqueous media. The prills can be contained within a gelatin capsule or blister. The capsule, like the ethyl-cellulose coating, dissolves when subjected to humid conditions or liquid aqueous media. The blister is typically not administered to a patient, but rather is opened or separated and the contents emptied therefrom for use.

One method of applying the coating to the prills utilizes a technique referred to in the art as panning. This technique was originally developed for sugar-coating and is discussed by S. C. Porter in "Coating of Pharmaceutical Dosage Forms", *Remington's Pharmaceutical Sciences*, 18th ed., A. R. Gennaro ed., Chapter 90, Mack Publishing Co., Easton Pa. (1990) pages 1666–1675.

U.S. Pat. No. 4,820,522 teaches the preparation of a sustained release acetaminophen preparation that includes hydroxyethyl cellulose as an excipient and povidone (polyvinyl pyrrolidone) as a granulating agent to form a shaped and compressed medicament. The resulting compressed medicament is provided in the form of a compressed tablet or as a layer of a multilayered tablet. In this composition, the povidone, hydroxyethyl cellulose and other ingredients bind the acetaminophen in a sustained release solid matrix. A composition of this patent is stated to further require the inclusion of a "wicking agent" such as microcrystalline cellulose to wick fluids into the matrix and also an "erosion promoter" such as pregelatinized starch. Although a composition of this patent provides sustained release of acetaminophen to normal adults, such a composition is tableted and as such, cannot provide the medication to a patient who has difficulty swallowing a tablet.

Another method of applying the coating is to coat the prills in a fluidized bed coating system. One typical type of system is the Wurster-type coater. In such a system, the fluidized bed coating vessel includes a bottom air inlet nozzle and a top or upper air outlet nozzle. The vessel typically has a divergent middle body expansion section. At about the expansion section, an air distributor plate spans the vessel. The distributor plate defines an upper reactor section and a lower feed section or air inlet plenum. The distributor plate includes orifices therein to effect a relatively even air distribution across the plate.

A partition-like, cylindrical coating column extends upwardly from above the distributor plate into the reactor section. The space between the coating column and the vessel walls defines a downflow bed. The coating column is positioned above the distributor plate to define a gap therebetween. The gap is sized to permit the inflow of material from the downflow bed, through the gap, and into the column. A spray nozzle extends from the feed section into the coating column from below the distributor plate. The spray nozzle is configured to provide a spray of coating material into the column.

In operation, the vessel is charged with a quantity of prills to be coated. The prills rest in the downflow bed, above the distributor plate, and surrounding the coating column.

Air is supplied to the vessel through the air inlet nozzle, into the inlet plenum. The air flow rate is selected to fluidize the downflow bed. In a typical arrangement, the air flow is selected to establish an incipiently fluidized bed in the region surrounding the coating column. In the incipiently fluidized bed, the pressure drop across the bed is equal to the gravitational force acting on the prill particles. Thus, the bed is minimally fluidized, and no voids or channels are formed therein.

The coating material is fed into the coating column through the spray nozzle. The upward flow of material and air through the column creates a low pressure zone at the bottom thereof which draws the prills from the downflow bed, through the gap between the distributor plate and the column. As the prills enter the column, they are accelerated upwardly by the spray and air flow.

In the coating column and the space thereabove, intimate mixing of the prills and the coating material occurs. As the coated prills rise in the column and lose energy, they are forced outward, away from the upward flow stream above the column. When the prills lose sufficient energy to be overcome by gravitational forces, they fall back down onto the downflow bed. The process is continued until the entire batch of charged prills is coated. When the process is complete, the prills are removed from the vessel for further processing. In some fluidized bed coating systems, a significant amount of drying of the prills occurs within the reactor vessel upper areas prior to the prills falling back into the downflow column.

The particular process controls, flow rates and pressures are typically determined by, among other things, the particle size and density, the coating type and coating thickness desired, the conditions of the infed air, and the drying requirements. The particular process control parameters for a given system will be recognized by those skilled in the art.

Although the Wurster-type coater has been used to provide coatings of all types for the drug industry, it is desirable to be able to more closely predict the time release rates or the dissolution profiles of such coated medication. Due to the nature of the distributor plate arrangement, it has been observed that the prills can agglomerate at the coating column. The agglomeration of prills can result in uneven coating thereof, which in turn, can produce less predictable dissolution rates.

Accordingly, there continues to be a need for an extended release acetaminophen composition that can be used to treat children and adults who have difficulty swallowing tablets or capsules, and that exhibits a predictable profile for the extended release of the acetaminophen over a period of time.

SUMMARY OF THE INVENTION

The present invention contemplates an extended release composition of acetaminophen in the form of generally spherical particles. The particles can be packaged in a gelatin capsule or a blister, and the contents administered in the gelatin capsule to adults that can swallow such capsules or the contents of the capsule or blister can be emptied therefrom and dispersed in an edible medium such as applesauce that can be swallowed by patients such as children that cannot swallow or have difficulty swallowing tablets, caplets or capsules.

The extended release acetaminophen composition comprises a plurality of discrete particles containing acetaminophen which, when contained within a gelatin capsule and assayed in a USP Apparatus I rotating basket at 50 rpm in 900 milliliters (mL) of phosphate buffer at pH 5.8 and 37° C. exhibits about 40 percent to about 53 percent acetaminophen released at one-half hour, about 50 percent to about 68 percent released at 45 minutes, about 57 percent to about 77 percent acetaminophen released at one hour, and about 82 percent to about 92 percent acetaminophen released at two hours. After six hours, the contemplated extended release acetaminophen exhibits substantially complete release.

Even though there appears to be overlap of the dissolution values at various times and subsequent, adjacent times, it is to be understood that a dissolution value within a stated range of values at a particular time increases from that dissolution value at a later time. As a consequence, even though the upper limit for a previously recited time frame can overlap with a lower limit from a subsequent time frame, an individual sample exhibits greater dissolution values until substantially complete dissolution is achieved.

Advantageously, a contemplated extended release acetaminophen composition provides an extended or sustained release profile in a particle-or prill- containing gelatin capsule or blister. A contemplated composition can thus be dispersed or sprinkled on, for example, food such as applesauce, so that it can be administered to a patient that, otherwise has difficulty taking, or could not take a "solid" tablet or caplet. Thus, the present extended release composition now provides long term analgesic administration for patients who otherwise could not obtain such relief.

It is to be understood that reference herein to gelatin capsule, capsule or blister is made only for the purpose of describing or providing various alternate packaging or "containing" vehicles for the composition of the present invention, and is not intended to limit the scope of the present invention. All such packaging or "containing" vehicles are thus within the scope of the present invention.

One exemplary composition comprises particles containing acetaminophen coated on sugar/starch seeds. All of these particles are free of a wicking agent and an erosion promoter as required and utilized in U.S. Pat. No. 4,820,522. The particles are present as a blend of both an immediate release and a controlled release form.

Preferably, the controlled release particles comprise a sugar/starch seed particle coated with a plurality of layers of acetaminophen and magnesium stearate that are bound with povidone. Most preferably, the acetaminophen-containing layers are coated with a plurality of layers of a mixture of povidone and magnesium stearate. In a contemplated composition, the weight ratio of acetaminophen to magnesium stearate in the controlled release particles is about 5:1 to about 10:1, and acetaminophen comprises about 70 to about 80 weight percent of the controlled release particles.

In a preferred composition, the immediate release particles also comprise sugar/starch seed particles, which seeds are coated with a plurality of layers of a mixture of acetaminophen, starch and cross-linked carboxymethyl cellulose bound with povidone. A preferred cross-linked carboxymethyl cellulose is croscarmellose NF. In a preferred composition, the immediate release particles contain acetaminophen, starch and cross-linked carboxymethyl cellulose in a weight ratio of about 13–16:1:1.5–2, respectively, and acetaminophen constitutes about 60–70 weight percent of the particles.

A preferred blend of the composition includes immediate release particles and controlled release particles in a weight ratio of about 1:1 to about 1:1.5, respectively.

The blend can also contain coated sugar/starch seeds that are free of acetaminophen. In one such blend, the immediate release particles, the controlled release particles and the coated sugar/starch seeds are present in a weight ratio of about 1:1–1.5:0.1–0.25.

Another exemplary composition comprises acetaminophen particles coated with each of a first, second and third layer, the first and third layers being hydroxypropyl cellulose and the second layer being ethylcellulose. Preferably, the weight ratio of each the first, second and third layers on a bead is about 1:4–6:1, respectively, and the acetaminophen constitutes about 92 to about 94 weight percent of each bead.

Most preferably, the beads are sized so that about 90 percent by weight pass through a 20 mesh sieve screen and about 90 percent by weight are retained on an 80 mesh sieve screen.

A process for treating a human patient that has difficulty swallowing acetaminophen in tablet, caplet or capsule form includes the steps of distributing an effective amount of the particles in a pharmaceutically acceptable palatable medium to form an acetaminophen particle-containing medium and administering the acetaminophen particle-containing medium to the human patient.

The present process is particularly contemplated for administering the composition to human patients that are about three months to about 14 years old, and particularly to children 2 to about 11 years old, including children that are febrile. However, the composition can be used by others that may have difficulty swallowing a tablet, caplet or capsule, or it can be used by those that do not have difficulty taking such "solid" non-dispersible medication forms.

Other features and advantages of the present invention will be apparent from the following detailed description, the accompanying drawings, and the appended claims.

BRIEF DESCRIPTION OF THE DRAWINGS

In the figures forming a portion of this disclosure.

DETAILED DESCRIPTION OF THE PREFERRED EMBODIMENTS

Figure 1:
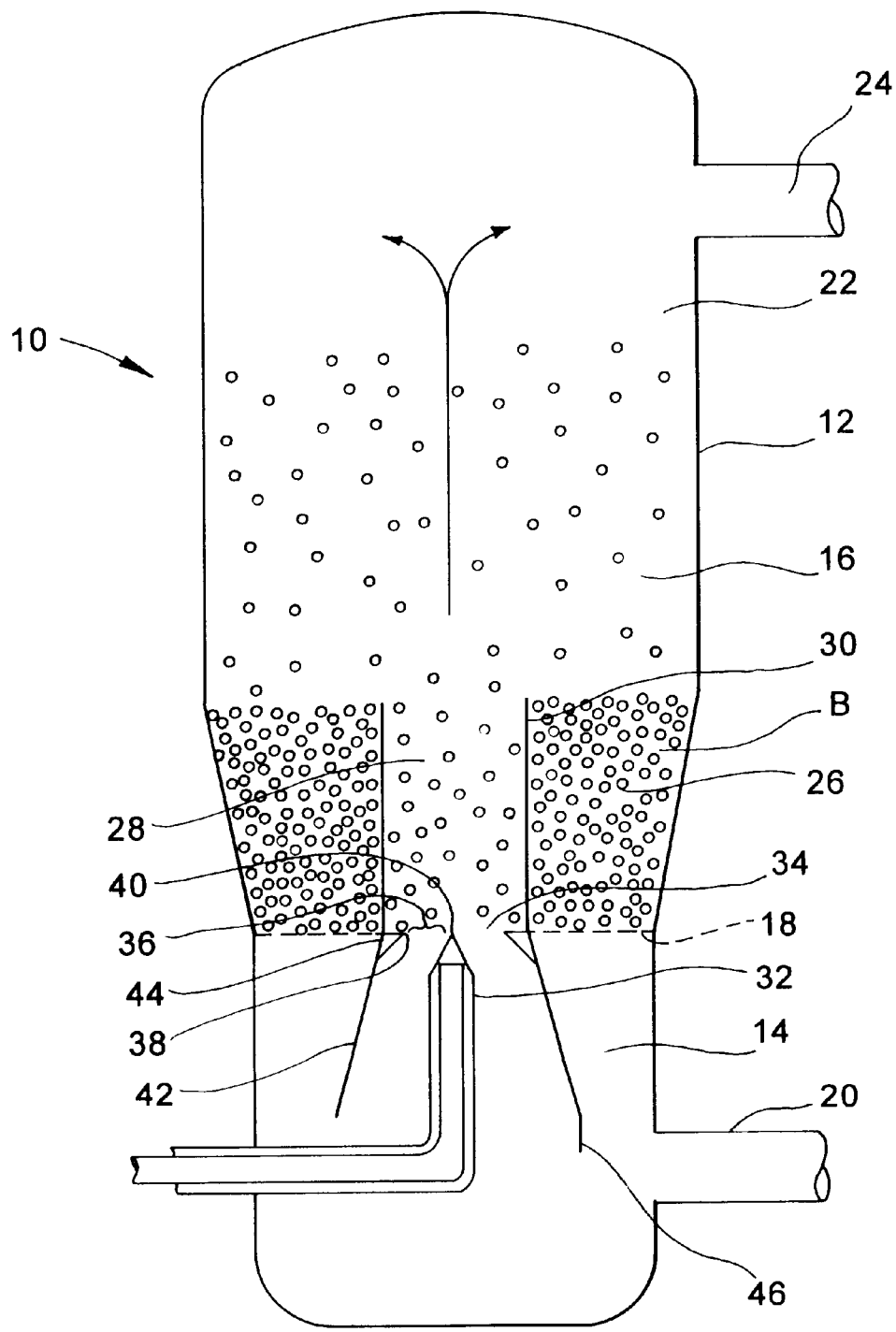
FIG. 1 is an illustration of fluidized bed coating system for preparing one exemplary extended release acetaminophen composition that embodies the principles of the present invention.

The present invention contemplates extended release acetaminophen. The acetaminophen is present as a composition of coated beads or particles (also referred to herein as pellets, prills or non-pareils). In a first exemplary form, the composition is a blend of beads or particles of both an immediate release form and a controlled or sustained release form. In a second exemplary form, the beads are generally spherical particles that are coated to provide extended release.

The composition, when contained within a gelatin capsule and assayed in vitro using the USP Apparatus I rotating basket protocol in 900 mL of phosphate buffer at a pH value of about 5.8 and at a temperature of about 37° C., exhibits about 40 percent to about 53 percent acetaminophen released at one-half hour, about 50 percent to about 68 percent acetaminophen released at 45 minutes, about 57 percent to about 77 percent acetaminophen released at one hour, and about 82 percent to about 92 percent acetaminophen released at two hours. After six hours, the contemplated extended release acetaminophen exhibits substantially complete release. Exemplary data for dissolution (e.g., release) and contemplated compositions are illustrated hereinafter.

Even though there appears to be overlap of the dissolution values at various times and subsequent, adjacent times, it is to be understood that a dissolution value within a stated range of values at a particular time increases from that dissolution value at a later time. As a consequence, even though the upper limit for a previously recited time frame can overlap with a lower limit from a subsequent time frame, an individual sample exhibits greater dissolution values until substantially complete dissolution is achieved.

A composition prepared in accordance with the present invention exhibits surprising and significant advantages over known acetaminophen preparations. Specifically, the composition exhibits substantial temperature depression in febrile children, and particularly at time periods after about 2½ hours after administration, compared to equally administered amounts of known immediate release acetaminophen preparations.

More surprisingly, an extended release acetaminophen composition prepared in accordance with the present invention exhibited sustained temperature depression compared to the known, commercial acetaminophen preparation, at a time period between about 4 hours and 6 hours, even after subsequent administration of the commercial preparation at 4 hours after initial administration.

As will be recognized by those skilled in the art, the sustained temperature depression, i.e., fever relief, has extreme benefits when administered to small children. Medical professionals, as well as parents and caregivers of small children know well that it is difficult if not impossible to have a small child swallow a pill or tablet. As such, it was previously unknown to provide an extended release acetaminophen composition to a child.

The present extended release acetaminophen composition provides such long term relief in a palatable form. The present composition permits administration of the medication to a child so that the child can benefit from the extended release formulation. This single dose administration can be extremely beneficial at night, when it may now be possible for a child to rest or sleep comfortably for a sufficiently long period of time, eight or more hours, while under the effects of the analgesic, as compared to having to wake the child to provide a second administration. Parents know all too well that a "good night's rest" can be beneficial to the comfort and recovery of an ill child.

A. The Composition

The contemplated composition is contained within a blister (or a gelatin capsule that can be orally administered as a capsule), that can be opened and the particles mixed with, for example, food such as applesauce, tapioca, flavored pudding or yogurt for those patients that have difficulty or cannot swallow a capsule, tablet or caplet.

Two exemplary compositions and the methods for preparing those compositions are described below. It is to be understood that the following descriptions are for illustrative purposes only and are not intended to limit the present invention to the exemplary compositions and methods for making the compositions provided herein.

Dissolution profiles or specifications have been developed for the present acetaminophen preparation based upon two accepted assaying techniques, namely the rotating basket and rotating bottle methods, which are discussed in detail below. The specifications include particularly preferred dissolution values based upon regulatory, i.e., FDA, requirements and "in-house" requirements as determined by the rotating basket method and "in-house" requirements as determined by the rotating bottle method.

Particularly preferred dissolution profiles are as shown in Tables 1 and 2 below.

TABLE 1

PARTICULARLY PREFERRED DISSOLUTION PROFILES FOR THE PRESENT EXTENDED RELEASE ACETAMINOPHEN PREPARATION AS MEASURED BY THE ROTATING BASKET METHOD

| Time (minutes) | Percent Dissolved (range) |
| --- | --- |
| 15 | 41 (33–49) |
| 30 | 47 (38–56) |
| 60 | 53 (43–64) |
| 120 | 65 (52–78) |
| 180 | 74 (59–89) |
| 240 | 82 (66–98) |
| 300 | NLT 90 |

TABLE 2

PARTICULARLY PREFERRED DISSOLUTION PROFILES FOR THE PRESENT EXTENDED RELEASE ACETAMINOPHEN PREPARATION AS MEASURED BY THE ROTATING BOTTLE METHOD

| Time (minutes) | Percent Release (range) |
| --- | --- |
| 15 | 50 (45–55) |
| 60 | 60 (54–66) |
| 120 | 70 (63–77) |
| 180 | 80 (72–88) |
| 240 | >90 |

Several of the dissolution value ranges presented above overlap such that an upper limit of a range at a particular time can have a higher percent dissolved than a lower limit of a range at a next later time. This is not to imply that the dissolution value is constant or reverses as time progresses. Rather, dissolution follows a substantially smooth curve with the total amount of acetaminophen being dissolved increasing over time until substantially all of the acetaminophen is dissolved.

i. First Exemplary Composition

A first exemplary composition is a blend of beads or particles of both an immediate release form and a controlled or sustained release from that contain acetaminophen coated on sugar/starch seeds. A preferred composition further includes inactive, acetaminophen-free particles or nonpareils (also referred to herein as placebo beads), such as coated sugar/starch seeds.

The first exemplary extended release acetaminophen composition includes a distribution of controlled release particles and immediate release particles that is made to effect a desired dissolution profile, that is dependent upon results of in-process testing. The batch amounts of the particles that are used to prepare the distribution are about 110 kg to about 140 kg of controlled release particles, about 90 kg to about 115 kg of immediate release particles and about zero kg to about 50 kg of placebo particles. Those skilled in the art will recognize that the weights of the various particles in each dosage; e.g., blister or capsule, can be varied depending upon the particular dosage desired, however, the weights of the immediate release and controlled release particles relative to one another typically remain relatively constant, to achieve that desired distribution and thus the desired dissolution profile.

It will also be recognized by those skilled in the art that the particular "dosage" provided in a given blister or capsule can vary depending upon the desired dosage. Anticipated desired dosages are 160 mg, 240 mg, 325 mg and 650 mg blisters.

The controlled release particles include acetaminophen, magnesium stearate and povidone disposed on a sugar/starch seed or core. A preferred sugar/starch seed is sugar spheres NF of between about 40 and 50 mesh, that contain not less than 62.5 percent and not more than 91.5 percent sucrose, calculated on the dry basis, the remainder consisting primarily of starch. (USP NF 1995 2313).

In a preferred form, the controlled release particles include a plurality of layers of acetaminophen and magnesium stearate on the sugar/starch seeds, which layers are bound with povidone. Most preferably, the acetaminophen-containing layers are coated with a plurality of layers of a mixture of povidone and magnesium stearate.

One preferred preparation of the controlled release particles includes acetaminophen in a weight ratio to magnesium stearate of between about 5:1 and about 10:1, and the acetaminophen is about 70 to about 80 weight percent of the controlled release particles.

A contemplated batch formula for the controlled release particles includes "Starter Beads" having a batch formula of about 100 kg of acetaminophen, about 5.3 kg of magnesium stearate NF, about 21.6 kg of sugar spheres NF (40 to 50 mesh) about 17 kg to about 30 kg of 15 percent povidone/isopropyl alcohol (IPA) stock solution, and about 47 kg to about 80 kg of isopropanol.

A 130.2 kg batch of the "Starter Beads" that is used to prepare the controlled release particles then has added thereto as additional coatings, about 5.85 kg to about 15.6 kg of magnesium stearate NF, about 2.4 L to about 6.4 L of isopropanol and about 2.4 L to about 6.4 L of 15 percent povidone/IPA stock solution. The amount (i.e., weight) of magnesium stearate, isopropanol and povidone/IPA solution applied as the coating are dependent upon the number of coatings required to meet specifications; i.e., the desired dissolution profile, as determined during in-process assays.

The immediate release particles are likewise formed of sugar/starch seeds having a plurality of layers of a mixture of acetaminophen, starch and a cross-linked carboxymethyl cellulose, preferably, croscarmellose sodium NF, that is bound with povidone. Preferably, the acetaminophen is present in a weight ratio to the starch and to the carboxymethyl cellulose of about 13–16:1:1.5–2, respectively, and the acetaminophen is about 60–70 weight percent of the immediate release particle.

A contemplated batch formula for the immediate release beads includes about 100 kg of acetaminophen, about 7.1 kg of cross-linked carboxymethyl cellulose, preferably croscarmellose NF, about 11.9 kg of starch NF, about 25.6 kg of sugar spheres NF (40 to 50 mesh) about 19 kg to about 34 kg of 15 percent povidone/IPA stock solution, and about 53 kg to about 91 kg of isopropanol.

The composition can further include, as part of the blend, placebo particles of coated sugar/starch seeds that do not contain acetaminophen. Preferably, the coated sugar spheres have a size of between about 30 and about 35 mesh.

A contemplated batch formula for the placebo particles includes about 10 kg of ethylcellulose 7-FP, about 50 kg of sugar spheres NF (30–35 mesh), about 1.2 kg of methylcellulose E-5, and purified water as needed.

A final distribution of immediate release particles, controlled release particles and placebo particles is made to effect a predetermined dissolution profile, and can be made to effect the particularly preferred dissolution profiles provided in Tables 1 and 2. The assay techniques are discussed hereinafter.

ii. Preparation of the First Exemplary Composition

The various particles that form the first exemplary composition; i.e., the immediate release particles, the controlled release particles and the placebo particles are each prepared in separate processes as presented below, and are subsequently blended together to form the present extended release acetaminophen composition.

a. Immediate Release Particle Preparation

The immediate release particles are prepared in two batches. A 100 kilogram (kg) quantity of acetaminophen, a 7.1 kg quantity of croscarmellose sodium NF, and an 11.9 kg quantity of starch NF, are each divided in half, and the three constituents are blended together to form two identical batches.

Each of the batches is milled through an 80 mesh screen using a mill such as a Fitzpatrick Mill. The two milled batches are then blended together to form a mixture, which is tested for composition in accordance with accepted quality assurance testing methods that are well-known by those skilled in the art.

The acetaminophen mixture is subsequently divided into three equal parts, with a first part remaining whole, and second and third parts each divided into lots of 50 percent, 30 percent and 20 percent.

A 25.6 kg quantity of 40–50 mesh sugar/starch seeds, e.g., sugar spheres NF, is placed in a stainless steel coating pan. An 80 liter (L) quantity of 5 percent povidone/IPA solution is prepared for spraying onto the particles.

The coating pan is started with the sugar spheres, onto which is sprayed an application (approximately 0.173 kg per application) of the povidone-alcohol solution, and onto which is sifted an application (approximately 0.32 kg) of the acetaminophen mixture from the first part (that part that remained whole). Sifting is done using a standard sifter. The spraying and sifting steps are continued until the first part of the mixture has been applied to the sugar spheres to form a batch of partially coated spheres.

The partially coated spheres are then divided into two equal lots, each lot being placed in a coating pan. Separately for each of the two lots, spraying of the povidone/IPA solution and sifting of the acetaminophen mixture as divided into the 50 percent lots continues until the 50 percent lots have been applied to the spheres. Following application of the 50 percent lots, the spheres can be screened using a 25 mesh screen if necessary.

The spraying of the povidone/IPA solution and sifting of the acetaminophen mixture as divided into the 30 percent lots commences and continues until the 30 percent lots have been applied to the spheres. The coated spheres can be rescreened using a 25 mesh screen.

Spraying of the povidone/IPA solution and sifting of the acetaminophen mixture continues using the mixture as divided into the 20 percent lots until the 20 percent lots have been applied to the spheres. At this point in the process, the entire quantity of the acetaminophen mixture has been applied to the spheres, and about 50 kg of the 5 percent povidone/IPA solution has been applied to the spheres.

A 7.5 percent povidone/IPA solution is prepared and applied to the spheres as a sealant. The sealed spheres are tumble dried for about one hour, weighed, and placed in an oven at about 122° F. for 24 hours. After drying, the spheres are screened through a 20 mesh screen and a 38 mesh screen to form the immediate release particles.

Those skilled in the art will recognize that the various mixtures and solutions are to be weighed, tested and assayed at selected stages during the process. Those skilled in the art will also recognize that the isopropanol as well as the isopropyl alcohol component of the povidone/IPA solution evaporate during the production process, and as such, their weights are not considered in the total particle weight of the final immediate release particles.

b. Controlled Release Particle Preparation

The controlled release particles are prepared in a similar process to that used for preparing the immediate release particles, employing a repeated spray and sift process.

"Starter Beads" are first prepared using a 100 kg quantity of acetaminophen and a 5.3 kg quantity of magnesium stearate that are each divided in half, and the two constituents blended together to form two identical batches. Each of the batches is milled through an 80 mesh screen using a mill such as a Fitzpatrick Mill. The two milled batches are then blended together to form one mixture, which is tested for composition in accordance with accepted quality assurance assaying methods.

The acetaminophen mixture is subsequently divided into three equal parts, with a first part remaining whole, and second and third parts each divided into lots of 50 percent, 30 percent and 20 percent.

A 21.6 kg quantity of 40–50 mesh sugar/starch seeds, such as sugar spheres NF, is placed in a stainless steel coating pan. An 80 liter (L) quantity of 5 percent povidone/IPA solution is prepared for spraying onto the particles.

The coating pan is started with the sugar spheres, onto which is sprayed an application (approximately 0.16 kg per application) of the povidone/IPA solution, and onto which is sifted an application (approximately 0.3 kg) of the acetaminophen mixture from the first part (that part that remained whole). Sifting is done using a standard sifter. The spraying and sifting steps continue until the first part of the mixture has been applied to the sugar spheres to form a batch of partially coated spheres.

The partially coated spheres are then divided into two equal lots, each lot being placed in a coating pan. Separately for each of the two lots, spraying of the povidone/IPA solution and sifting of the acetaminophen mixture divided into 50 percent lots continues until the 50 percent lots have been applied to the spheres. Following application of the 50 percent lots, the spheres can be screened using a 25 mesh screen if necessary.

Spraying of the povidone/IPA solution and sifting of the acetaminophen mixture as divided into the 30 percent lots commences and continues until the 30 percent lots have been applied to the spheres. The coated spheres can be rescreened through a 25 mesh screen if necessary.

The spraying of the povidone/IPA solution and sifting of the acetaminophen mixture commences and continues using the mixture divided into 20 percent lots until the 20 percent lots have been applied to the spheres. At this point in the process, the entire quantity of the acetaminophen mixture has been applied to the spheres, and about 50 kg of the 5 percent povidone/IPA solution has been applied to the spheres.

A 7.5 percent povidone/IPA solution is prepared and applied to the spheres as a sealant. Sealed spheres are tumble-dried for one hour, weighed, and placed in an oven at about 122° F. for 24 hours. After drying, the spheres are screened using a 20 mesh screen and a 38 mesh screen, which screened beads form the "Starter Beads".

An additional 7.5 percent povidone/IPA solution is prepared, and the "Starter Beads" are divided into two equal panloads. A quantity of magnesium stearate necessary to coat the particles is then prepared.

The beads are wetted by applying a quantity (approximately 0.7 L) of the povidone/IPA solution and are coated by applying about 0.8 kg of magnesium stearate. The coated starter beads are dried for about 15 minutes.

The steps of wetting with povidone/IPA solution and coating with magnesium stearate continue until a desired number of "coats" has been achieved. The coated beads are assayed and a release pattern is obtained during in-process testing. The "coating" can then be repeated until a desired release pattern is achieved, that is, until the beads are within specifications.

After coating is complete, the beads are placed in an oven and dried at ambient temperature for about 16 to about 24 hours. The beads, which are now the controlled release particles, are sampled, tested and screened using a 20 mesh screen.

c. Placebo Particle Preparation

The placebo particles are also prepared in a "spray and sift" process, similar to the controlled and immediate release particles. Two 2.5 kg quantities and one 5 kg quantity of ethylcellulose (Ethocel® 7-FP) are dispensed. A 1.2 kg quantity of methylcellulose (Methocel® E-5) and 50 kg of 30–35 mesh sugar/starch seeds, such as sugar spheres NF are also dispensed.

The methylcellulose is prepared as a coating suspension in accordance with manufacturers instructions and is left to stand for at least 8 hours prior to use.

The sugar spheres are placed in a stainless steel coating pan, the pan is started, and the spheres are wetted with the methylcellulose suspension (approximately 0.211 kg per application) using a pressurized gun. Ethylcellulose powder (approximately 0.37 kg per application) is then sifted onto the wetted spheres using a standard sifter.

The wetting and sifting steps are continued until the first (5 kg) portion of ethylcellulose is applied. The spheres are then screened using a 24 mesh screen and the wetting and sifting steps continued until the spheres reach 24 mesh on a 30 mesh screen.

The spheres are tumbled in the coating pan, weighed and assayed in accordance with accepted quality assurance assay methods that are well-known by those skilled in the art. Subsequent to assaying, the spheres are placed in an oven and dried at about 122° F. for at least 24 hours. After drying, the spheres (now placebo particles or beads) are screened using 20 mesh and 30 mesh screens.

iii. Second Exemplary Composition

In a second exemplary composition, the acetaminophen is present as generally spherical particles that are coated to provide extended release. The generally spherical particulate acetaminophen utilized herein itself exhibits a relatively narrow range of sizes. As an example, about one percent of the particles are retained on a 40 mesh sieve, whereas at least about 88 percent are retained on an 80 mesh sieve. U.S. Sieve series sizes are utilized herein for sieve mesh sizes. More preferably, about 90 percent or more of the acetaminophen particles pass through a 40 mesh sieve and are retained on an 80 mesh sieve. A typical lot of granular acetaminophen available from Mallinckrodt Chemical of St. Louis, Mo., under the designation Acetaminophen USP Special Granular Code 1617 is said by that manufacturer to be retained at about 0.1 percent on a 40 mesh sieve about 80 percent on a 60 mesh sieve and about 98 percent being retained on an 80 mesh sieve. These acetaminophen particles are preferred, but suitable material can be obtained from other commercial sources or can be prepared by sieving.

The acetaminophen particles constitute the cores of the extended release composition, and those core particles are each coated with three separate coating layers that are referred to herein as the first, second and third layers, respectively, proceeding from the acetaminophen particle surface outwardly in the order mentioned. The first layer is hydroxypropyl methylcellulose, the second is ethylcellulose, and the third is hydroxypropyl methyl cellulose again. The individual coated particles are also generally spherical in shape.

Those three layers each homogeneously cover the particle surface as well as each earlier coating layer so that each coating is uniformly distributed over the surface it covers. The coatings are applied from aqueous media as described hereinafter to provide weight add-ons in a ratio of about 1:4–6:1, respectively in their order of application. Those weight ratios to each other are also the approximate weight percentage add-ons of each coating to the final weight of the composition so that a contemplated sustained-release acetaminophen composition contains about 4 to about 6 weight percent of the second layer, or about 5 weight percent of the total composition as solids.

Hydroxypropyl methylcellulose can be obtained from a number of commercial sources. A particularly useful and preferred hydroxypropyl cellulose is available under the trademark OPADRYO® from the Colorcon Division of Berwind Pharmaceutical Services, Inc. of West Point, Pa. (Colorcon). The material sold under the designation "YS-1-7472 clear" is particularly preferred herein, and is a powder said to contain hydroxypropyl methylcellulose and polyethylene glycol.

Ethylcellulose can also be obtained from a number of commercial sources. The particularly useful and preferred material for use herein is available under the trademark SURELEASE® E-7-19010 from Colorcon. This material is an off-white turbid liquid dispersion said to contain water, ethylcellulose, fractionated coconut oil, oleic acid and ammonium hydroxide at a pH value of 9.5–11.5. This product is said to contain 24–26 percent solids.

The acetaminophen is thus present at about 92 to about 94 weight percent of the composition, with the second coating being present at about 4 to about 6 weight percent. The first and third coatings are present at about one weight percent each.

The coated acetaminophen particles are sized so that more than 90 percent pass through a 20 mesh sieve screen, and about 90 percent are retained on a 60 mesh sieve screen. An exemplary screening result for a contemplated composition is shown below wherein a minus sign (−) indicates passage through the sieve and a plus (+) indicates retention.

| Sieve | Percentage |
|---|---|
| +18 | 0.0 |
| −18+20 | 0.9 |
| −20+40 | 33.6 |
| −40+50 | 43.6 |
| −50+60 | 13.6 |
| −60+80 | 6.4 |
| −80 | 1.8 |

The above-noted preferred layering materials have been used together, alone and in several combinations to coat powdered medicaments such as theophylline and acetaminophen. However, neither the amounts utilized herein, nor their sequenced combination of layers, nor the unexpected results obtained using those amounts in that sequence of layers have been reported.

Thus, for example, Technical Data Sheet PTA-96 (10-88) of Colorcon reports use of a 10 weight percent add-on of SURELEASE® 0601-96 to form controlled-release theophylline produced using two different fluid-bed reactors. Colorcon Technical Data Sheet PT-35 (10-92) describes use of an 80/20 (dry solids basis) single coating of SURELEASE®/OPADRY® to coat tablets in a pan-coating technique. Similarly, Colorcon Technical Data Sheet PT-38 (10-92) discloses the use of a coat of SURELEASE®, followed by an 80/20 coat of SURELEASE®/OPADRY® (as above) and then a coat of SURELEASE®/sodium lauryl sulfate (93.5:6.5 solids) to provide a 15 percent weight add-on and taste-masking to acetaminophen granules, with the coated granules being admixed with other ingredients to more than three times their original weight to ultimately form compacted tablets.

Technical Data Sheet PT-30 (10-92) of Colorcon discloses a controlled-release phenylpropanolamine hydrochloride composition. Here, the drug was first coated with a 12 percent add-on of OPADRY® (YS-3-7065), followed by one percent OPADRY® (YS-1-7472), 10 percent SURELEASE® (E-7-7050), and another one percent OPADRY® (YS-1-7472).

iv. Preparation of the Second Exemplary Composition

FIG. 1 illustrates a fluidized bed coating system 10 for preparing the coated particles of the second exemplary acetaminophen composition. The fluidized bed system 10 includes a fluidized bed vessel 12 defining an air inlet region or plenum 14 and a coating region 16. The inlet plenum 14 and coating region 16 are separated by an air distributor plate 18 that spans the vessel body 18. The inlet plenum 14 is in communication with an air inlet nozzle 20 through which air is supplied to the vessel 12. At the upper portion (as indicated at 22) of the coating region 16, the vessel 12 includes an air outlet 24.

The vessel body 12 has a generally diverging or expansion region (indicated at 26) that begins above the air distributor plate 18 and extends into the coating region 16. The diverging region 26 defines a volume for accommodating a downflow bed B of the acetaminophen particles.

The vessel 12 includes a coating column 28 that is defined by an upwardly extending cylindrical partition 30 that extends upward from the distributor plate 18. The coating column 28 provides a region for coating the acetaminophen particles, and further provides a weir-type arrangement to retain the acetaminophen particles within the downflow bed B, segregated from the particles in the coating column 28.

A spray nozzle 32 extends into the coating column 28 from below the distributor plate 18. The distributor plate 18 has an opening 34 therein to accommodate penetration of the nozzle 32. The opening 34 defines a nozzle gap 36 between the inner edge 38 of the plate 18 and the nozzle body 32. The nozzle 32 extends upward, through the opening 34, with a tip 40 thereof about coplanar with the distributor plate 18.

The vessel 12 includes a swirl accelerator 42 extending downward from the distributor plate 18, at about the inlet nozzle 20 opening. The accelerator 42 extends into the inlet plenum 14. The swirl accelerator 42 has a generally frustoconical shape that tapers inward toward the distributor plate 18. At about the juncture of the accelerator 42 and the distributor plate 18, the accelerator 42 includes an inwardly tapered directing element 44. The accelerator 42 also includes a deflector plate 46 extending downwardly therefrom to deflect and distribute the inflowing air throughout the plenum 14.

The coating system 10 is operated in a batch mode. In use, the vessel 12 is charged with a quantity of particles that comes to rest in the downflow bed B. Air is introduced into the air inlet plenum 14, and flows upward through the distributor plate 18 through the bed of acetaminophen particles. The upward flow of air fluidizes the particles in the downflow bed B.

Although the flow of air upward through the plate 18 is sufficient to fluidize the bed of particles it is not so great as to create a void space above the distributor plate 18 or through the bed. In practice, the air flow rate is selected to establish an incipiently fluidized bed, in which the pressure drop across the bed B is equal to the gravitational force on the acetaminophen particles. In such a process, the bed B is minimally fluidized. It will be recognized by those skilled in the art that a fluidized bed often exhibits fluid-like properties. That is, the "bed" assumes the shape of the container in which it is placed, and tends to flow in a fluid-like manner.

A spray of coating material in an aqueous medium is injected from the spray nozzle 32 into the coating column 28. The spray comprises a quantity of coating material, as well as a predetermined quantity of warm air. The hydrodynamic force of the coating exiting the spray nozzle 32 creates a region of low pressure to the sides of and behind the nozzle 32, at about the distributor plate 18. The low pressure region draws air from the inlet plenum 14 into the accelerator 42, past the nozzle 32, and into the coating column 28. The accelerator 42 imparts a swirling motion to the air that is drawn therethrough. The swirling motion imparts additional rotational velocity and turbulence to the inflowing air.

The coating material, along with the air drawn therein is forced upward into the coating column 28. The acetaminophen particles that have been fluidized in the downflow bed B are drawn toward and through the gap 36 between the column 28 and the distributor plate 18. At the gap 36, the particles are drawn into the flowing stream in the column 28 by the forces exerted on the particles by the low pressure region surrounding the nozzle 32. As the particles enter the coating column 28, they are accelerated upwardly, into the flowing stream. Essentially, the particles exhibit a spouting-like flow condition in the coating column 28.

As the spray of coating material and the particles travel upward in the coating column 28, intimate mixing occurs. The intimate mixing among the air, the coating material and the particles provides an evenly coated, readily predetermined thickness of coating on the particles. As the "wet", coated particles rise through the expansion region 26, they are subjected to intimate contact with the relatively dry, warm upflowing air from the bed B, and to reduced pressure conditions in the upper portions of the vessel 12. The combination of air contact and low pressure drives off moisture from the coating and thus facilitates drying of the particles and minimizes the formation of clumps or aggregates of coated particles that might otherwise occur.

It has been observed that in the present system 10, the acetaminophen particles are individually drawn into the coating column 28 and upward therethrough. This is quite unlike known coating systems in which the particles tend to agglomerate as they are drawn into the coating column. This is due in part to the rotational velocity and additional turbulence imparted by the swirl accelerator on the inflowing air.

Moreover, it has also been observed that in known systems, the flow patterns within the coating column, and thus the coating characteristics on the acetaminophen particles, are dominated by the flow of the particles. This is due, in part, to the agglomeration of the particles as they flow upwardly in the coating column. Conversely, in the present system 10, the particles are individually drawn into the coating column 28. Thus, the flow patterns within the coating column 28, and the resulting coating characteristics on the particles, are dominated by the air flow through the column 28.

Advantageously, because the air flow patterns, rather than the particle flow patterns dominate the coating column stream, coating of the particles is more finely controlled. The finely controllable coating process tends to facilitate the ability to produce evenly and predictably coated acetaminophen particles whose dissolution rate in an aqueous medium can thereby be relatively easily controlled. In a preferred embodiment, coating of the acetaminophen particles is carried out in a PRECISION COATER® brand fluidized bed coating system, manufactured by Aeromatic-Fielder Ltd. of Eastleigh, Hampshire, U.K., and available from GEA Niro, Inc. of Columbia, Maryland.

Physio-chemical and Efficacy Studies

Physio-chemical and efficacy studies were conducted in order to determine the dissolution rates and to determine the effectiveness of the present extended release composition. The physio-chemical studies were conducted in vitro and included rotating basket assays. Once suitable in vitro rates for these dissolutions were in hand, dissolution of the exemplary extended release acetaminophen compositions prepared in accordance with the present invention were then compared to a known, commercially available acetaminophen product, namely Tylenol® Extended Relief Caplets (in 650 mg dose), as an external standard.

Efficacy studies were conducted in vivo to determine the comparative effectiveness for producing long term temperature depression or relief of the present acetaminophen composition relative to a known commercially available acetaminophen product, namely Children's Tylenol® Immediate Release Elixir.

a. In Vitro Dissolution Studies

The dissolution studies included comparative studies of the dissolution rates of two exemplary acetaminophen compositions of the present invention to the dissolution rates of Tylenol® Extended Relief Caplets (650 mg). The studies included rotating basket tests that were carried out in accordance with accepted methods as provided in USP 23/NF 18, United States Pharmacopeial Convention, Inc., Rockville, Md. 1791 (1994).

b. Rotating Basket Assays

The rotating basket assays were carried out in accordance with USP 23/NF 18 accepted procedure. The testing apparatus for each of the samples; i.e., Tylenol® Extended Relief Caplets and the acetaminophen composition of the present invention was a USP Apparatus I, rotating at 50 rpm, using a medium of 900 mL of phosphate buffer at a pH of 5.8 and a temperature of 37° C. Six samples of each lot of the products (i.e., the Tylenol® Extended Relief Caplet product and the first exemplary contemplated acetaminophen composition) were assayed at times of 10, 20, 30, 45, 60, 120, 360, 480 and in some cases 720 minutes. Filters used were Hanson Probe 10μm.

The test medium was analyzed for UV absorbance of the test solution vs. standard acetaminophen (APAP), USP at 244 nm. The samples (indicated as Smpl in the following Tables 3–6) assayed included the first exemplary acetaminophen composition in one dosage of 650 mg (Table 3), and two sets of samples of the Tylenol® Extended Relief Caplet product (Lot #MFM437 and Lot #PEM910, in 4 and 5, respectively). The results of the of the rotating basket assays are shown below in Tables 3, 4 and 5.

Two samples of the second exemplary acetaminophen composition (Lot N) were assayed. The results of the Lot N assays are provided in Table 6, as a range of the dissolution values determined, along with a summary of the comparison of the results of the Tylenol® Extended Relief Caplet product (Lot #PEM910) of samples and the first exemplary acetaminophen preparation (Lot #EXPT9236).

TABLE 3

PERCENT DISSOLUTION OF THE PRESENT EXTENDED RELEASE ACETAMINOPHEN COMPOSITION (650 mg, Lot # EXPT 9236)

| Time (Min.) | Smpl 1 | Smpl 2 | Smpl 3 | Smpl 4 | Smpl 5 | Smpl 6 | Mean |
|---|---|---|---|---|---|---|---|
| 10 | 13.6 | 10.7 | 11.5 | 11.4 | 15.1 | 13.6 | 12.6 |
| 20 | 27.5 | 33.6 | 28.9 | 26.5 | 30.3 | 26.7 | 28.9 |
| 30 | 37.9 | 40.6 | 36.9 | 38.1 | 39.0 | 36.7 | 38.2 |
| 45 | 48.3 | 50.7 | 46.9 | 45.7 | 48.9 | 48.1 | 48.1 |
| 60 | 57.0 | 59.5 | 55.1 | 54.0 | 58.7 | 56.7 | 56.8 |
| 120 | 83.0 | 83.8 | 79.2 | 78.5 | 82.6 | 82.9 | 81.7 |
| 360 | 101.1 | 100.9 | 98.4 | 97.8 | 100.0 | 101.3 | 99.9 |
| 480 | 104.7 | 105.8 | 102.4 | 102.5 | 102.3 | 103.8 | 103.6 |
| 720 | 103.7 | 104.5 | 104.7 | 102.8 | 104.1 | 106.2 | 104.2 |

TABLE 4

PERCENT DISSOLUTION OF TYLENOL ® EXTENDED RELIEF CAPLET (1 CAPLET @ 650 mg., Lot # MFM437)

| Time (Min.) | Smpl 1 | Smpl 2 | Smpl 3 | Smpl 4 | Smpl 5 | Smpl 6 | Mean |
|---|---|---|---|---|---|---|---|
| 10 | 29.9 | 33.4 | 41.6 | 39.7 | 42.0 | 41.8 | 38.1 |
| 20 | 48.5 | 49.0 | 51.1 | 50.6 | 49.8 | 51.0 | 50.0 |
| 30 | 53.3 | 56.3 | 54.0 | 51.2 | 53.5 | 56.7 | 54.2 |
| 45 | 58.5 | 57.2 | 62.9 | 57.2 | 59.7 | 62.9 | 59.7 |
| 60 | 63.6 | 60.5 | 68.0 | 63.1 | 64.2 | 67.2 | 64.4 |
| 120 | 73.7 | 75.6 | 74.4 | 80.1 | 74.0 | 74.1 | 75.3 |
| 360 | 102.5 | 100.5 | 100.9 | 102.1 | 101.6 | 99.1 | 101.1 |
| 480 | 102.8 | 100.8 | 98.7 | 99.9 | 100.7 | 100.2 | 100.5 |
| 720 | 103.2 | 101.4 | 105.4 | 102.3 | 103.5 | 102.5 | 103.1 |

TABLE 5

PERCENT DISSOLUTION OF TYLENOL ® EXTENDED RELIEF CAPLET (1 CAPLET @ 650 mg., Lot # PEM 910)

| Time (Min.) | Smpl 1 | Smpl 2 | Smpl 3 | Smpl 4 | Smpl 5 | Smpl 6 | Mean |
|---|---|---|---|---|---|---|---|
| 10 | 44.0 | 45.4 | 44.1 | 47.9 | 49.0 | 46.6 | 46.1 |
| 20 | 51.8 | 50.7 | 53.3 | 53.3 | 52.6 | 53.8 | 52.6 |
| 30 | 58.2 | 57.9 | 56.2 | 57.0 | 59.3 | 59.4 | 58.0 |
| 45 | 61.9 | 63.1 | 60.8 | 60.9 | 62.3 | 63.2 | 62.0 |
| 60 | 64.8 | 65.5 | 65.0 | 64.0 | 65.4 | 66.2 | 65.1 |
| 120 | 79.5 | 79.5 | 77.7 | 76.9 | 79.8 | 78.2 | 78.6 |
| 360 | 103.2 | 104.3 | 99.6 | 103.1 | 100.1 | 102.1 | 102.1 |
| 480 | 104.8 | 102.7 | 101.9 | 103.1 | 101.5 | 100.9 | 102.5 |

TABLE 6

CONDENSED SUMMARY OF RESULTS OF ROTATING BASKET DISSOLUTION COMPARISON OF THE FIRST (Lot # EXPT9236) AND A RANGE FOR THE SECOND (Lot N) EXEMPLARY EXTENDED RELEASE ACETAMINOPHEN COMPOSITIONS and TYLENOL ® EXTENDED RELIEF CAPLETS (Lot # PEM910) IN PERCENT DISSOLVED

| Time (min.) | First Exemplary Comp. (Lot # EXPT9236) | Second Exemplary Comp. (Lot N) | Tylenol ® |
|---|---|---|---|
| 10 | 12.6 | 17.9–20.0 | 38.1 |
| 20 | 28.9 | 34.4–37.9 | 50.0 |
| 30 | 38.2 | 49.2–52.6 | 54.2 |
| 45 | 48.1 | 64.7–67.9 | 59.7 |
| 60 | 56.8 | 75.3–76.8 | 64.4 |
| 120 | 81.7 | 91.4–91.9 | 75.3 |
| 360 | 99.9 | 99.4–102.3 | 101.1 |
| 480 | 103.6 | 103.3–104.6 | 100.5 |

As can be seen from the data of Tables 3–6, the contemplated acetaminophen preparations exhibited more controlled and slower sustained release, particularly at early time periods, than did the Tylenol® Extended Relief Caplet product. At about 20 minutes after commencement of the test, 50 percent of the Tylenol® Extended Relief Caplet product had dissolved. After one hour almost two-thirds of the Tylenol® Extended Relief Caplet product had dissolved, and over 75 percent by two hours. In contrast, a contemplated acetaminophen preparation when contained within a gelatin capsule had achieved about 40 percent to about 53 percent acetaminophen dissolution at one-half hour, about 50 percent to about 68 percent dissolution at 45 minutes, about 57 percent to about 77 percent acetaminophen dissolution at one hour, and about 82 percent to about 92 percent acetaminophen dissolution at two hours. After six hours, the contemplated extended release acetaminophen composition achieved substantially complete dissolution.

Those in vitro dissolution rates were measured in vitro in 900 mL of phosphate buffer at pH 5.8 and at a temperature of 37° C. in a USP Apparatus I rotating basket at 50 rpm.

Even though there appears to be overlap of the dissolution values of the present contemplated acetaminophen composition at various times and subsequent, adjacent times, it is to be understood that a dissolution value within a stated range of values at a particular time increases from that dissolution value at a later time. As a consequence, even though the upper limit for a previously recited time frame can overlap with a lower limit from a subsequent time frame, an individual sample exhibits greater dissolution values until substantially complete dissolution is achieved.

Surprisingly, the in vitro dissolution rate of a contemplated sustained release composition is substantially the same as that observed for the in vitro sorption rate for the same composition.

Rotating Bottle Assay Techniques

Rotating bottle assays were carried out in order to establish dissolution profiles, such as the particularly preferred dissolution profiles as illustrated in Table 2, for the contemplated acetaminophen composition. The rotating bottle assays were carried out in accordance with a variant of NF XIV, American Pharmaceutical Association, Washington, D.C. 985 (1974), procedure. The assay apparatus was a rotating bottle apparatus, rotating at 30 rpm, using a medium of 60mL of modified gastric fluid prepared in accordance with the aforenoted NF XIV. The assay conditions varied from the accepted NF XIV procedure in that the pH of the fluid used (gastric fluid) differed from that of the NF XIV procedure, and the duration of the assay that was carried out (one hour) differed from that of the NF XIV procedure.

In Vivo Studies

Randomized trial studies were conducted to determine whether a contemplated acetaminophen composition administered as a single dose for an 8 hour period was as efficacious in reducing fever as Children's Tylenol® Immediate Release Elixir, administered in two doses, in febrile children between the ages of 2 and 11 having initial temperatures $\geq 101.0°$ F. Administration was carried out using a contemplated acetaminophen composition at an initial administration time and a placebo at four hours post initial administration, and the Tylenol® Immediate Release Elixir product at initial administration and at four hours post initial administration. It is noted that the Tylenol® Immediate Release Elixir product labeling states that four hours should elapse between administrations.

The study group included 120 children; 59 received the Tylenol® Immediate Release Elixir product and 61 received a contemplated acetaminophen composition. Some of the children were also treated, concomitantly, with antibiotics.

Temperature measurements were recorded at pre-dose, ½, 1, 1½, 2, 3, 4, 5, 6, 7 and 8 hours after initial administration. Temperatures were measured using an Exergen LighTouch Infrared Ear Thermometer, which uses an arterial heat balance method.

Figure 2:
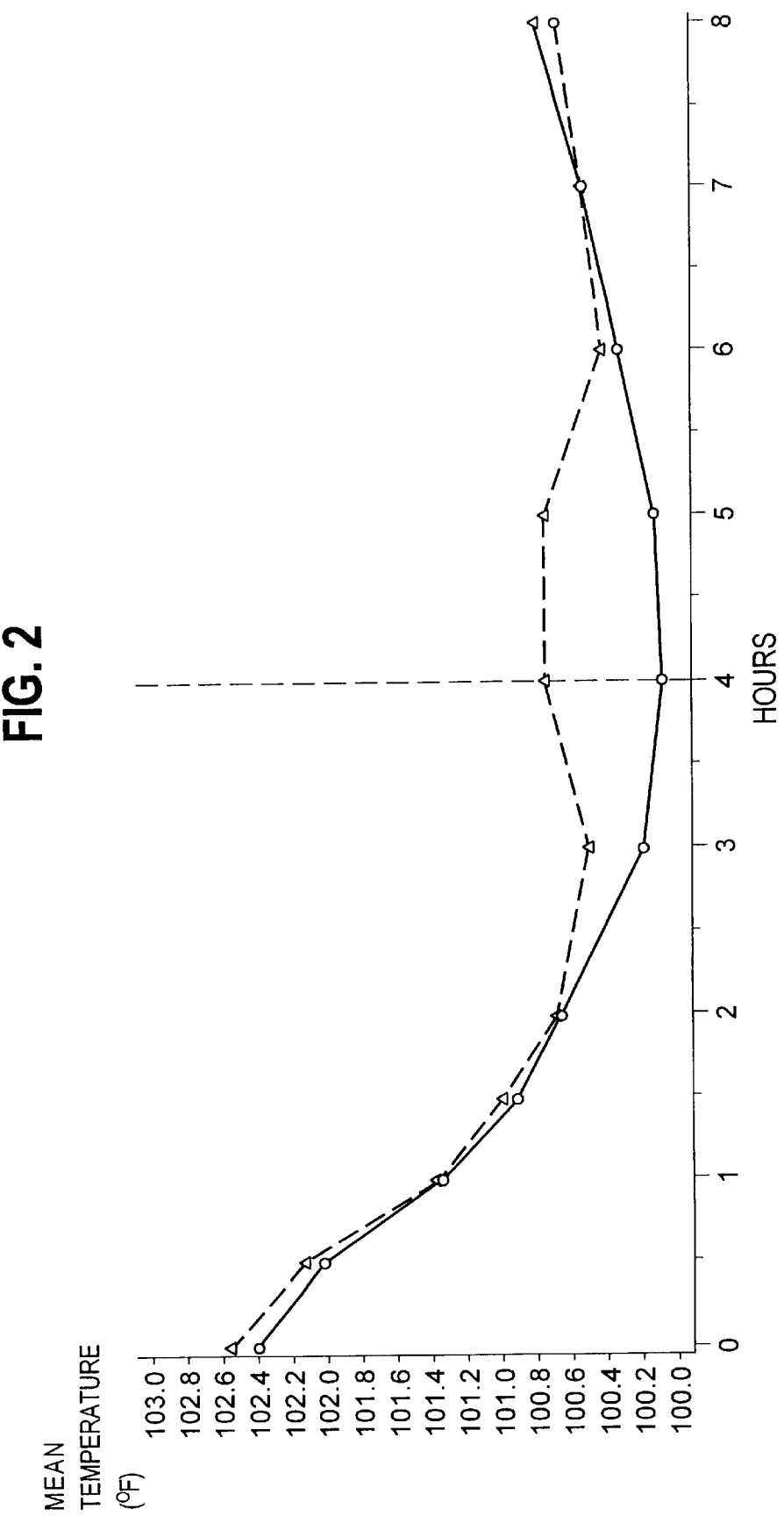
FIG. 2 is graphic illustration of the overall results of a randomized trial comparing the present acetaminophen composition and Children's Tylenol® Immediate Release Elixir in febrile children, showing the mean temperature in degrees Fahrenheit as a function of time, in which the circles represent data for a contemplated acetaminophen composition and the triangles represent data for the Tylenol® Immediate Release Elixir product.
Figure 3:
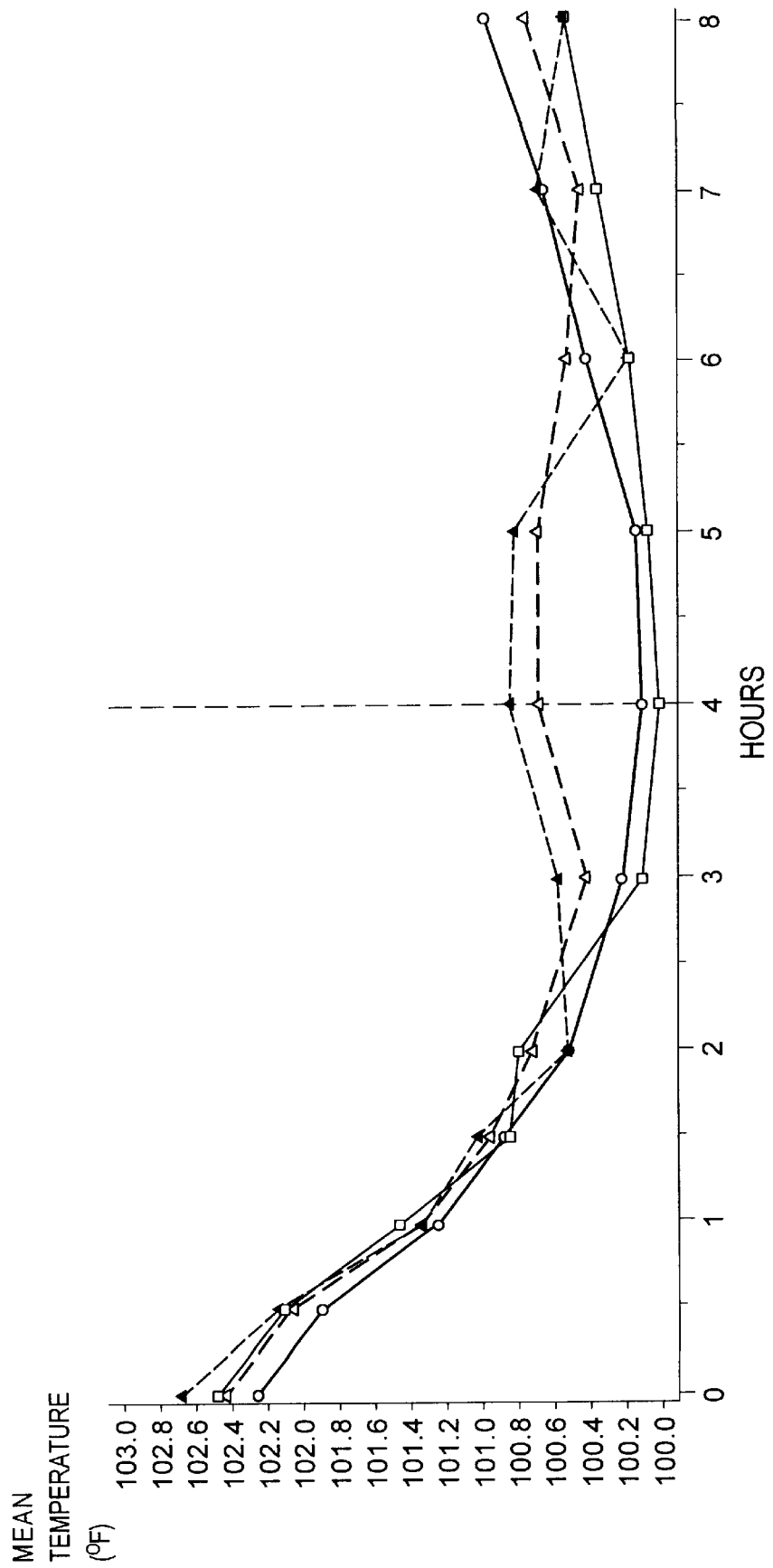
FIG. 3 is a graphic illustration of the data of FIG. 2 in which the data are segregated by the concomitant use and nonuse of an antibiotic. Here, the filled and empty circles represent data for a contemplated acetaminophen composition with and without, respectively, the concomitant use of an antibiotic, whereas the filled and empty triangles represent data for the Tylenol® Immediate Release Elixir product with and without, respectively, the concomitant use of an antibiotic.
Figure 4:
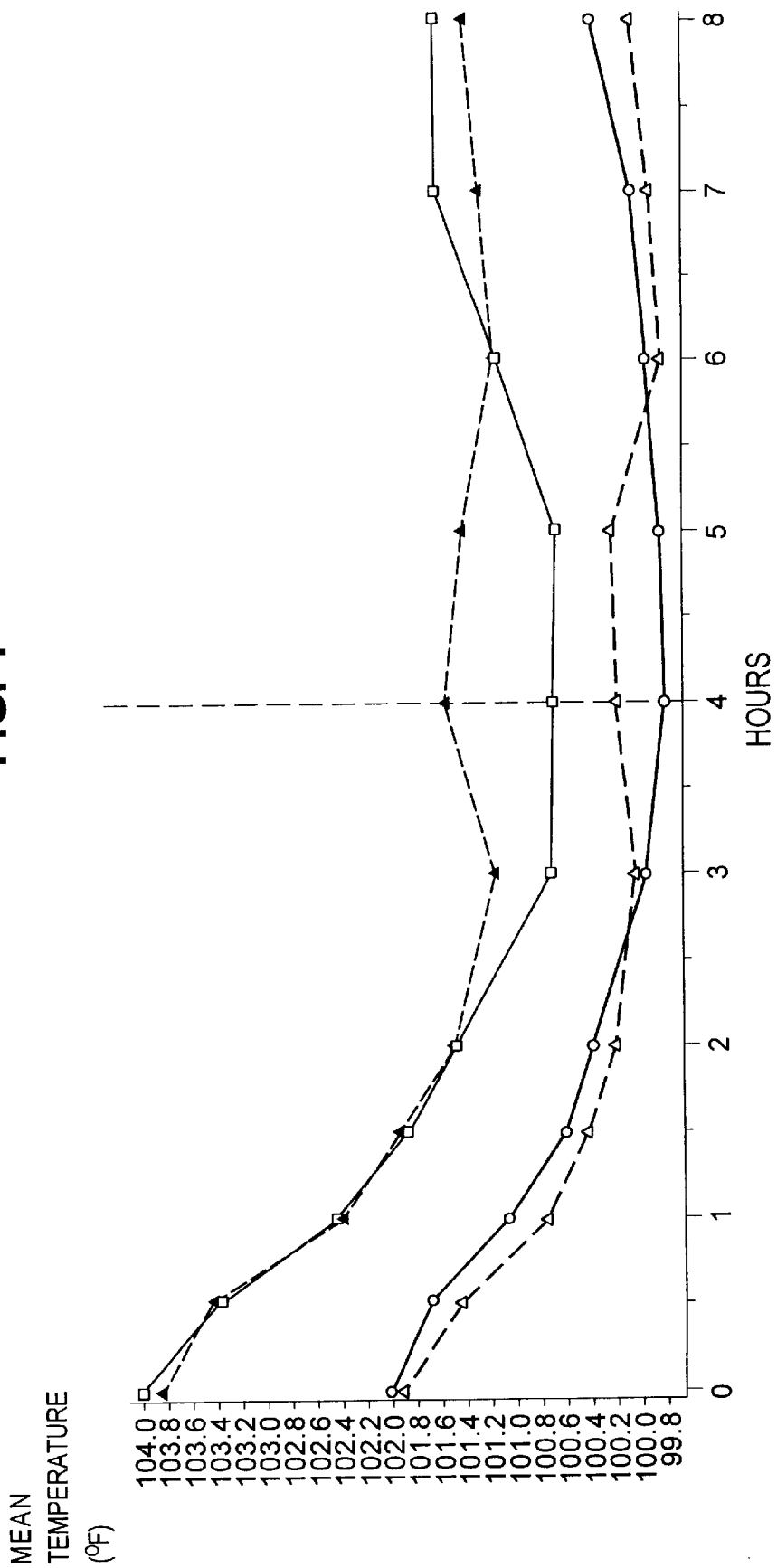
FIG. 4 is a graphic illustration of the data of FIG. 2 in which the data are segregated by high and low baseline temperatures. In this figure, the filled and empty circles represent data for a contemplated acetaminophen composition at high and low baseline temperatures, respectively, and the filled and empty triangles represent data for the Tylenol® Immediate Release Elixir product at high and low baseline temperatures, respectively.

The results of the studies are shown in FIGS. 2–4. In all of the figures, the circles (filled and empty) represent the data for a contemplated acetaminophen composition (preparation) and the triangles (filled and empty) represent the data for the Tylenol® Immediate Release Elixir product. FIG. 2 shows the overall results in mean temperature as a function of time, and includes all of the results, including children with both moderate and severe initial fevers (low and high baseline temperatures, respectively), as well as children that were concomitantly administered antibiotics. FIG. 3 shows the mean temperature over time and is segregated by antibiotic use. FIG. 4 shows the mean temperature over time and is segregated by high and low baseline temperatures.

As can be seen from the results, in every case, the effect of the Tylenol® Immediate Release Elixir product began to decrease after about two hours, as indicated by the decline in temperature reduction rate after two hours and an increase in temperature levels after about three hours.

Significantly, even after re-administration at four hours after initial administration (shown by the dotted vertical line at 4 hours), the temperature-reducing effect of the Tylenol® Immediate Release Elixir product required about two hours until it achieved an effect that approached the same or an equivalent effect to that of a contemplated acetaminophen composition. That is, a contemplated acetaminophen composition exhibited a significantly greater ability to reduce and maintain reduced temperatures in a single dosage than an equivalent amount of the Tylenol® Immediate Release Elixir product. This result was quite unexpected because the bioavailability of both materials was equivalent.

Referring to FIG. 3, wherein the filled circles and triangles indicate the data for concomitant antibiotic use for a contemplated acetaminophen composition and the Tylenol® Immediate Release Elixir product, respectively, and the empty circles and triangles indicate the data for no antibiotic use for a contemplated acetaminophen composition and the Tylenol® Immediate Release Elixir product, respectively, it is readily apparent that use of a contemplated acetaminophen composition, with or without concomitant antibiotic use, exhibited increased and prolonged fever reduction compared to an equivalent amount of the Tylenol® Immediate Release Elixir product. This result was also unexpected.

Surprisingly, in viewing the concomitant antibiotic data of the Tylenol® Immediate Release Elixir product, compared to a contemplated acetaminophen composition, a contemplated composition exhibited an increase in fever reduction with the concomitant antibiotic use, whereas the Tylenol® Immediate Release Elixir product showed a lesser effect when used with antibiotics. For example, referring to FIG. 3, at 3 hours post initial administration, a contemplated acetaminophen composition when used with antibiotics exhibited a mean temperature reduction of about 2.4° F. (from about 102.5° F. to about 100.1° F.), whereas the Tylenol® Immediate Release Elixir product exhibited a temperature reduction of only about 2.1° F. (from about 102.7° F. to about 100.6° F.)

This difference is more dramatic at four hours after administration (at the time of the second Tylenol® Immediate Release Elixir product administration), where it can be seen that the effectiveness of the Tylenol® Immediate Release Elixir decreased, whereas the effectiveness of a contemplated acetaminophen composition increased, and the mean temperature reduction differences were about 2.5° F. (from about 102.5° F. to about 100.0° F.) for a contemplated acetaminophen composition and about 1.9° F. (from about 102.7° F. to about 100.8° F.) for the Tylenol® Immediate Release Elixir product. It is interesting to note that at all times during the study, with respect to concomitant antibiotic use, the mean temperature data for a contemplated acetaminophen composition was lower than that for the Tylenol® Immediate Release Elixir product.

The data that are illustrated in FIG. 4 are segregated by high and low baseline temperatures for a contemplated acetaminophen composition and the Tylenol® Immediate Release Elixir product (illustrated as filled circles for a contemplated acetaminophen composition and filled triangles for the Tylenol® Immediate Release Elixir product, at high baseline temperatures and as empty circles for a contemplated acetaminophen composition and empty triangles for the Tylenol® Immediate Release Elixir product, at low baseline temperatures).

As can be seen from the data, a contemplated acetaminophen composition exhibited a significantly greater temperature reduction in children with high baseline temperatures at both three and four hours after administration, of about 3.2° F. (from about 104° F. to about 100.8° F.) compared to the Tylenol® Immediate Release Elixir product, which exhibited a temperature decrease of only about 2.6° F. and 2.2° F., respectively at three and four hours (from about 103.8° F. to about 101.2° F. at three hours, which subsequently increased to about 101.6° F. at four hours). Thus, a contemplated acetaminophen composition exhibited considerable effectiveness in reducing high baseline temperatures reductions compared to the Tylenol® Immediate Release Elixir product. Again, this was an unexpected result.

At lower baseline temperatures, a contemplated acetaminophen preparation exhibited greater temperature reduction, with a greatest difference at four hours, where the present acetaminophen preparation exhibited a temperature reduction of about 2.1° F. (from about 102.0° F. to about 99.9° F.) compared to the Tylenol® Immediate Release Elixir product, which showed a temperature reduction of about 1.6° F. (from about 101.9° F. to about 100.3° F.).

The results of the in vivo study data were statistically assessed using Fisher's Exact Test for categorical data and using Wilcoxon Rank Sum Test for continuous variables. Efficacy end points were compared using the Wilcoxon Rank Sum Test and a linear regression model was used to assess the treatment effect adjusted for potential confounders.

Statistically significant differences in mean temperatures between a contemplated acetaminophen composition (single dose) and the Tylenol® Immediate Release Elixir product (two doses) were shown at four and five hours after initial administration that favored a contemplated acetaminophen composition. There was generally a greater magnitude of temperature reduction in patients administered a contemplated acetaminophen composition than those administered the Tylenol® Immediate Release Elixir product with high baseline temperatures than in those with low baseline temperatures. However, the patterns of temperature reduction in patients with high and low baseline temperatures were similar to each other and similar to the patterns seen in the overall analysis.

The mean area-under-curve (AUC) values from initial administration to four hours post administration for all patients; i.e., overall results, were generally greater for a contemplated acetaminophen composition than those for the Tylenol® Immediate Release Elixir product.

As provided herein, the present extended release acetaminophen composition provides long term, extended relief in a palatable form. A contemplated acetaminophen composition permits administering the medication to a child so that the child can benefit from an extended release formulation. This can be extremely beneficial at night, so that a child can rest or sleep comfortably for a sufficiently long period of time, eight or more hours, while under the effects of the analgesic if the child is in pain, or under the effects of the antipyretic if the child is febrile. Parents know all too well that a "good night's rest" can be beneficial to the comfort and recovery of an ill child.

Another trial study was conducted to determine the efficacy of a contemplated acetaminophen composition compared to a known analgesic (Tylenol® Extended Relief caplets), and a placebo, over an eight hour period, for the relief of pain from oral surgery, specifically, the surgical removal of impacted third molars. In this study, 125 patients were randomly administered 1300 mg of a contemplated acetaminophen composition, 1300 mg of Tylenol® Extended Relief caplets or a placebo.

The results of this study indicate that patients to whom the contemplated acetaminophen composition and the Tylenol® Extended Relief Caplet product were administered, experienced mean pain intensity difference scores that were significantly higher than those patients to whom the placebo were administered. No significant pair-wise differences were exhibited between the contemplated acetaminophen composition and the Tylenol® Extended Relief Caplet product.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. An extended release acetaminophen composition comprising a plurality of discrete particles containing acetaminophen which, when contained within a gelatin capsule and assayed in a USP 23/NF 18 Apparatus I rotating basket at 50 rpm in 900 mL of phosphate buffer at pH 5.8 and 37° C.

exhibits about 40 percent to about 53 percent acetaminophen dissolution at one-half hour, about 50 percent to about 68 percent dissolution at 45 minutes, about 57 percent to about 77 percent acetaminophen dissolution at one hour, about 82 percent to about 92 percent acetaminophen dissolution at two hours and about 100 percent dissolution at six hours.

2. The extended release acetaminophen composition according to claim 1 comprising particles containing acetaminophen coated on sugar/starch seeds, said particles present as a blend of both an immediate release and a controlled release form.

3. The extended release acetaminophen composition according to claim 2 wherein said controlled release particles comprise a sugar/starch seed particle coated with a plurality of layers of acetaminophen and magnesium stearate that are bound with povidone, and said acetaminophen-containing layers are coated with a plurality of layers of a mixture of povidone and magnesium stearate.

4. The extended release acetaminophen composition according to claim 3 wherein the weight ratio of acetaminophen to magnesium stearate in said controlled release particles is about 5:1 to about 10:1, and acetaminophen comprises about 70 to about 80 weight percent of said controlled release particles.

5. The extended release acetaminophen composition according to claim 2 wherein said immediate release particles comprise a sugar/starch seed particle coated with a plurality of layers of a mixture of acetaminophen, starch and cross-linked carboxymethyl cellulose bound with povidone.

6. The extended release acetaminophen composition according to claim 5 wherein said immediate release particles contains acetaminophen, starch and cross-linked carboxymethyl cellulose in a weight ratio of about 13–16:1:1.5–2, respectively, and acetaminophen constitutes about 60–70 weight percent of the particles.

7. The extended release acetaminophen composition according to claim 2 wherein said immediate release particles and said controlled release particles are present in said blend at a weight ratio of about 1:1 to about 1:1.5, respectively.

8. The extended release acetaminophen composition according to claim 2 wherein said blend also contains coated sugar/starch seeds that are free of acetaminophen.

9. The extended release acetaminophen composition according to claim 8 wherein said immediate release particles, said controlled release particles and said coated sugar/starch seeds are present in said blend at a weight ratio of about 1:1–1.5:0.1–0.25.

10. The extended release acetaminophen composition according to claim 1 wherein said discrete particles comprise an acetaminophen particles coated with each of a first, second and third layer, wherein said first and third layers are comprised of hydroxypropyl cellulose and said second layer is ethylcellulose.

11. The extended release acetaminophen composition according to claim 10 wherein the weight ratio of each said first, second and third layers on a bead is about 1:4–6:1, respectively, and said acetaminophen constitutes about 92 to about 94 weight percent of each bead.

12. The extended release acetaminophen composition according to claim 10 wherein said beads are sized so as that about 90 percent by weight pass through a 20 mesh sieve screen and about 90 percent by weight are retained on an 80 mesh sieve screen.

13. A process for treating a human patient that has difficulty swallowing acetaminophen in tablet, caplet or capsule form that comprises the steps of:

(a) distributing an effective amount of the acetaminophen coated particles of claim 1 in a palatable medium to form an acetaminophen particle-containing medium; and (b) administering said acetaminophen particle-containing medium to said human patient.

14. The process according to claim 13 wherein said human patient is a child about 3 months to about 14 years old.

15. The process according to claim 14 wherein said child is febrile.

16. A process for treating a febrile child that comprises the steps of:

(a) distributing an effective amount of the acetaminophen coated particles of claim 1 in a palatable medium to form an acetaminophen particle-containing medium; and (b) administering said acetaminophen particle-containing medium to said febrile child.

17. The process according to claim 16 wherein said febrile child about 3 months to about 14 years old.

18. An extended release acetaminophen composition comprising a plurality of discrete particles containing acetaminophen coated on sugar/starch seeds, said particles being present as a blend of both an immediate release and a controlled release form that are blended at a weight ratio of about 1:1 to about 1:1.5, respectively, which, when contained within a gelatin capsule and assayed in a USP 23/NF 18 Apparatus I rotating basket at 50 rpm in 900 mL of phosphate buffer at pH 5.8 and 37° C., exhibits about 40 percent to about 53 percent acetaminophen dissolution at one-half hour, about 50 percent to about 68 percent dissolution at 45 minutes, about 57 percent to about 77 percent acetaminophen dissolution at one hour, about 82 percent to about 92 percent acetaminophen dissolution at two hours and about 100 percent dissolution at six hours.

* * * * *